United States Patent [19]

Ihlenfeld, III

[11] Patent Number: 4,667,682
[45] Date of Patent: May 26, 1987

[54] CARDIAC AMBULATORY MONITOR

[75] Inventor: William Ihlenfeld, III, Runnemede, N.J.

[73] Assignee: Creative Medical Systems, Inc., Cherry Hill, N.J.

[21] Appl. No.: 751,016

[22] Filed: Jul. 2, 1985

[51] Int. Cl.⁴ ............................................. A61B 5/04
[52] U.S. Cl. .................................. 128/711; 128/702; 128/705; 128/706
[58] Field of Search ....................... 128/689, 702–706, 128/708, 710–711

[56] References Cited

U.S. PATENT DOCUMENTS

| | | | |
|---|---|---|---|
| 3,513,833 | 5/1970 | Finch et al. | 128/706 |
| 3,648,689 | 3/1972 | Dominy | 128/710 |
| 3,650,263 | 3/1972 | Kowalski et al. | 128/706 |
| 3,773,038 | 11/1973 | Smith et al. | 128/706 |
| 3,858,574 | 1/1975 | Page | 128/689 |
| 3,978,856 | 9/1976 | Michel | 128/705 |
| 4,022,192 | 5/1977 | Laukien | 128/706 |
| 4,034,745 | 7/1977 | Bloom | 128/706 |
| 4,083,366 | 4/1978 | Gombrich | 128/706 |
| 4,184,487 | 1/1980 | Peyer | 128/710 |

Primary Examiner—William E. Kamm
Attorney, Agent, or Firm—Norman E. Lehrer

[57] ABSTRACT

An ambulatory arrhythmia detection and ECG recorder senses both tachycardia and bradycardia conditions and activates a tape recorder to record the ECG for a period of 15 seconds after an arrhythmia is detected. Tachycardia and bradycardia conditions are sensed by converting the QRS component signals of the ECG into a pulse train which is a real time representation of the patient's actual heartbeat and then measuring the time between pulses utilizing two different oscillator controlled counter circuits. The first circuit indicates a tachycardia condition if the time between pulses is less than 500 milliseconds (120 beats per minute) or some other time preset by a doctor and the second circuit indicates a bradycardia condition if the time between pulses is greater than 1200 milliseconds (50 beats per minute) or some other time preset by a doctor. The recorder may also record the ECG waveform for 15 seconds upon a manual activation thereof and at preset intervals such as every half hour or hour in accordance with a preset program.

13 Claims, 2 Drawing Figures

CARDIAC AMBULATORY MONITOR

BACKGROUND OF THE INVENTION

The present invention is directed toward a heart monitoring device and more particularly toward such a device which is intended to be carried by a patient and which detects arrhythmias and records the patient's ECG in response thereto.

Cardiac monitoring apparatuses which detect arryhthmias have been known for many years. These are described, for example, in U.S. Pat. Nos. 3,144,019; 3,552,386; 3,587,563; 3,608,545; 3,823,708; 3,824,990; 3,881,467; 4,231,374; 4,261,370 and 4,457,315. It is known that the detection of two particular arrhythmias, tachycardia or high heartbeat rate and bradycardia or low heartbeat rate, are useful in providing information to a physician concerning the general condition of a patient's heart. Many of the foregoing patents describe systems for detecting tachycardia and/or bradycardia.

The systems described in the above patents are, for the most part, relatively sophisticated and are useful in a hospital environment and particularly in a cardiac care unit. These systems are not well suited for portable monitoring of ambulatory patients.

The apparatus described in U.S. Pat. No. 4,457,315 is specifically designed for use as a portable battery operated device to be carried by an ambulatory patient. While the device proposed in this patent would provide the desired benefits of portability not available with many of the prior monitors, it is not believed that the patented device has met with much succcess. This may be due to the relative complexity of the circuit thereby making the same relatively expensive. Furthermore, the circuit of the device shown in this patent utilizes an average over a series of heartbeats in order to determine the existence of an arrhythmia and, accordingly, is not capable of substantially instantaneously providing such an indication.

SUMMARY OF THE INVENTION

The present invention is designed to overcome the deficiencies of the prior art described above to provide a highly reliable and inexpensive cardiac ambulatory monitor. The ambulatory arrhythmia detection and ECG recorder of the present invention senses both tachycardia and bradycardia conditions and activates a tape recorder to record the ECG for a period of 15 seconds after an arrhythmia is detected. Tachycardia and bradycardia conditions are sensed by converting the QRS component signals of the ECG into a pulse train which is a real time representation of the patient's actual heartbeat and then measuring the time between pulses utilizing two different oscillator controlled counter circuits. The first circuit indicates a tachycardia condition if the time between pulses is less the 500 milliseconds (120 beats per minute) or some other time preset by a doctor and the second circuit indicates a bradycardia condition if the time between pulses is greater than 1200 milliseconds (50 beats per minute) or some other time preset by a doctor. The recorder may also record the ECG waveform for 15 seconds upon a manual activation thereof and at preset intervals such as every half hour or hour in accordance with a preset program.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

DETAILED DESCRIPTION OF THE PREFERRED EMBODIMENT

Figure 1:
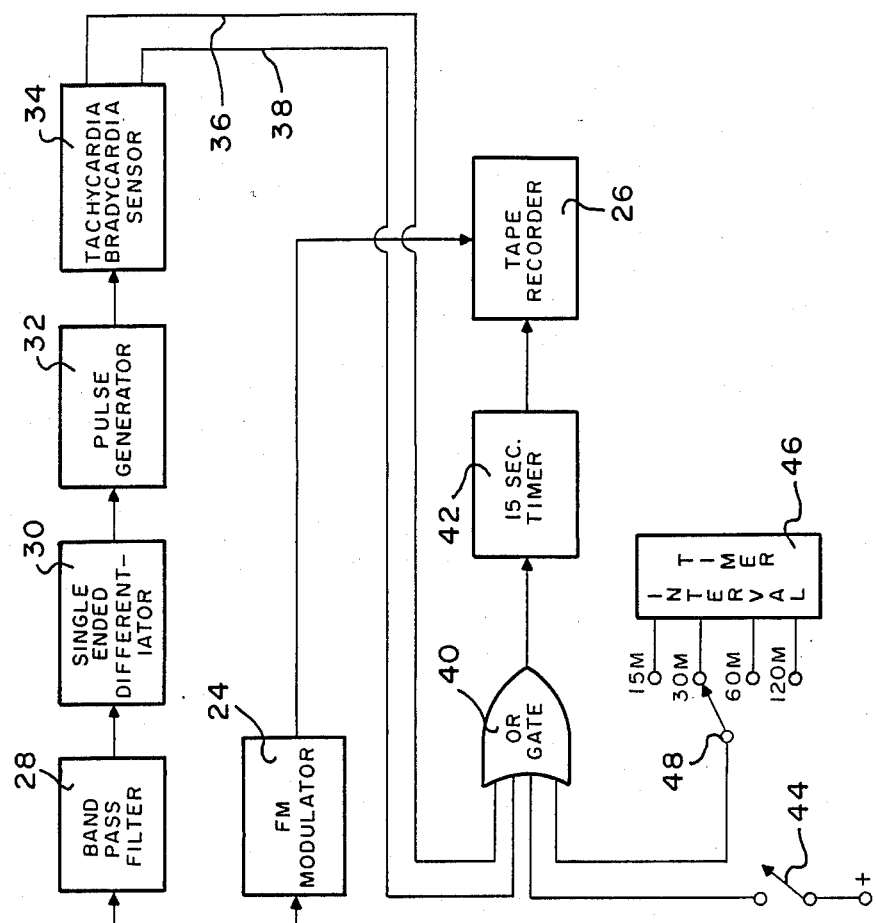
FIG. 1 is a schematic representation shown primarily in block form of a cardiac ambulatory monitor constructed in accordance with the principles of the present invention.

Referring now to the drawings in detail wherein like reference numerals are used in the drawings to designate like elements, there is shown in FIG. 1 an overall schematic view primarily in block form of an ambulatory heart monitor constructed in accordance with the principles of the present invention and designated generally as 10. The monitor 10 is intended to be battery operated and relatively compact and light so that it can be carried by a patient in a pocket or attached to the patient's belt or the like.

Three electrodes 12, 14 and 16 are adapted to be positioned on a patient's body. Preferably, they are arranged in what is commonly referred to as a "Marquette arrangement" wherein the positive electrode is positioned over the heart, the ground electrode is positioned over the left shoulder and the negative electrode is positioned over the right shoulder. The three electrodes develop an electrical signal which is indicative of the patient's cardiac rhythm as is well known in the art. The three electrodes are connected to an input amplifier 18 which is a dual differential amplifier producing a single ended amplified signal of the cardiac rhythm. In the preferred embodiment, amplifier 18 has an amplification factor of approximately 10 times.

The output of amplifier 18 is fed to high-pass filter 20 which filters out the low frequency base line drift due to physical activity which results from impedance mismatching between the three electrode leads. The output of high-pass filter 20 is then fed to the low-pass filter 22 which removes artifacts above the frequency range of approximately 125 Hz.

The output from low-pass filter 22, which should now be a substantially true representation of the patient's ECG signal, is frequency modulated by modulator 24, the output of which is connected to the audio input of tape recorder 26. Tape recorder 26 is preferably of the micro or mini cassette type and may either be built directly into the same housing which carries the remaining components of the ambulatory heart monitor 10 or it may be a separate cassette recorder which is also carried by the patient. As will be explained more fully hereinafter, the frequency modulated ECG signal is constantly applied to the audio input terminal of the tape recorder 26. However, the tape recorder drive is only activated for 15-second intervals at selected times or when certain conditions are met. Accordingly, the frequency modulated ECG signal is only recorded during these 15-second intervals.

The output of low-pass filter 22 is also fed into bandpass filter 28 which removes the P and T waves from the ECG leaving only the QRS complex which is between approximately 5 Hz and 40 Hz. Thereafter, the signal is fed to single-ended differentiator 30 which differentiates the QRS complex leaving a waveform representing the true frequency components of the QRS signal. The output of differentiator 30 is fed into pulse generator 32 which is essentially a voltage detector which produces a positive voltage pulse which falls in the frequency spectrum of the QRS frequency levels. Therefore, the output from the pulse generator 32 is a digital pulse whose analog relationship is effectively centered around the frequency components of the QRS complex. In other words, pulse generator 32 generates a pulse train in real time relationship with the ECG wherein each pulse represents the actual occurrence of a QRS complex and, thus, a different heartbeat.

The pulse train from pulse generator 32 is fed to the tachycardia and bradycardia condition sensing circuit 34, the details of which will be described more fully hereinafter. A normal heart rate is approximately 80 beats per minute. If circuit 34 senses the pulse train from pulse generator 32 to be well in excess of 80 beats per minute, for example, above 120 beats per minute, a first control signal indicating a tachycardia condition will appear on tachycardia output 36 of circuit 34. Similarly, if circuit 34 senses that the pulse train from pulse generator 32 is considerably below the normal heart rate, for example, below 50 beats per minute, a bradycardia condition control signal will appear on bradycardia output 38 of circuit 34.

The tachycardia control output 36 and bradycardia control output 38 of circuit 34 are connected to different control inputs of OR gate 40. Thus, if a control signal appears on either control line 36 or 38, the OR gate will conduct initiating the 15-second timer 42. Timer 42 will activate the drive circuit of the tape recorder 26 so that the tape recorder will now record the actual ECG for the 15 seconds next following the occurrence of a control signal to the OR gate 40. Thereafter, the timer 42 will automatically deactivate tape recorder 26.

The OR gate 40, which in combination with the timer 42 functions as the recorder controller, has two other control inputs. One of these control inputs is connected to a manually operable momentary contact push button switch 44. Should the patient believe that he has sensed an arrhythmia or should he merely wish to test the device, he simply depresses switch 44 whereby the recorder controller OR gate 40 and timer 42 will activate the tape recorder 26 for 15 seconds.

The physician may also wish to monitor the patient's ECG periodically during the course of a day whether or not any arrhythmias have been sensed. In order to accomplish this, an interval timer 46 is also connected to one of the control inputs of the OR gate 40. Interval timer 46 has a plurality of selectable outputs and generates a pulse every 15 minutes, 30 minutes, 60 minutes or 120 minutes depending on which output is selected by interval selector switch 48. Thus, if the physician places interval selector switch 48 at 30 minutes, for example, the tape recorder 26 will record the ECG every 30 minutes during the day. Each recording will, of course, be 15 seconds long as determined by the timer 42.

Figure 2:
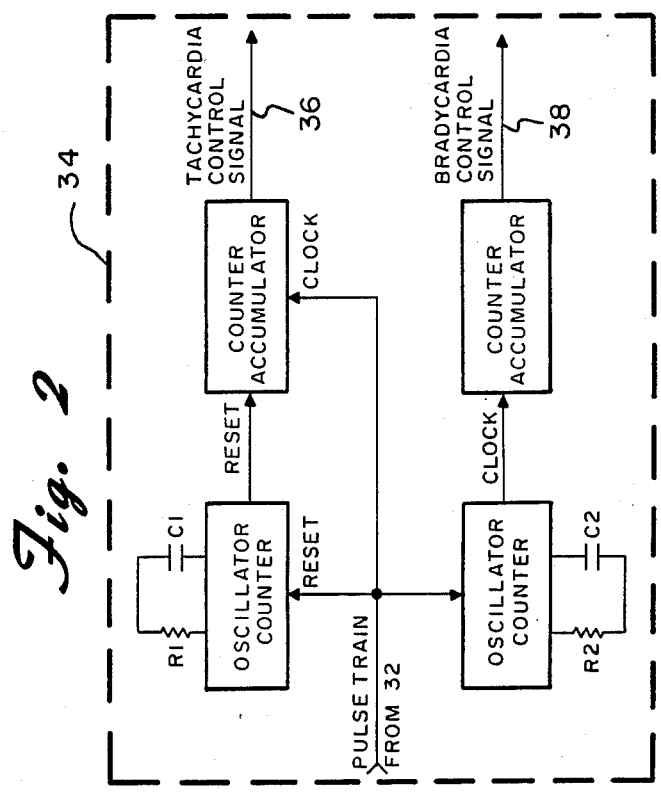
FIG. 2 is a schematic diagram showing the tachycardia and bradycardia condition sensing circuits of FIG. 1.

The tachycardia and bradycardia condition determining circuit 34 will now be described in further detail with reference to FIG. 2. The upper portion of FIG. 2 is utilized to determine a tachycardia condition whereas the lower portion of the circuit of FIG. 2 determines a bradycardia condition.

The tachycardia condition sensing circuit includes a first oscillator controlled counter 50 which counts at a first predetermined rate. As is known in the art, the counting rate will be determined by the value of the resistor R1 and capacitor C1. The oscillator counter 50 will count to a predetermined number and generates a first output signal each time it reaches the predetermined number. The pulse train from pulse generator 32 is connected to the reset input of the oscillator counter 50 so that the counter is reset upon the receipt of each pulse from the pulse generator 32.

The output signal from the oscillator counter 50 is connected to the reset of a first counter accumulator 52. Thus, each time the oscillator counter 50 reaches the predetermined number which is preset therein, an output signal is generated which resets the accumulator 52 back to zero. The accumulator 52 also has a clock input which is connected to the output of pulse generator 32. Each time a pulse is received from the pulse generator 32, the counter accumulator 52 is incremented by one. A control signal is generated at the output of accumulator 52, i.e. on line 36, whenever the accumulator is incremented to a first preset number.

From the foregoing, it should be readily apparent to those skilled in the art that the accumulator 52 will be incremented past one only if the time between the pulses from pulse generator 32 is less than the time it takes for the oscillator counter 50 to reach the predetermined number to which it is to count. Otherwise, the counter 50 will reset the accumulator 52 to zero before it can be incremented to two.

If a tachycardia condition is determined by the physician to be a heartbeat rate of above 120 beats per minute, then the predetermined number to which the counter 50 is to count and the rate at which it is to count are set so that the counter 50 reaches the predetermined number in 500 milliseconds which is equivalent to 120 beats per minute. In order to reduce errors, it is preferred that the counter 50 be a multistage counter and that the oscillator have a frequency of approximately 31,000 cycles per second. In this case, the first predetermined number to which the counter 50 must count in order to generate an output signal would be approximately 15,500. It is preferred that either the frequency rate or predetermined number or both be manually adjustable by the physician so that a tachycardia condition can be set to be above or below 120 beats per minute as desired. This can be accomplished by making R1 and/or C1 variable or by providing means for allowing the physician to change the taps on the multistage counter.

While the counter accumulator 52 can be preset to generate a control signal each time a pair of pulses from the pulse generator 32 occur in less than the 500 milliseconds or other predetermined time, it is preferred that the accumulator 52 must be incremented to a higher preset number such as four in order to avoid errors. It is not uncommon, even with normal heartbeat rates, for there to occasionally be a pair of pulses having a time duration between them of less than 500 milliseconds. With the accumulator 52 set at four, four pulses in a row having a time duration between them of less than 500 milliseconds must occur before a tachycardia control signal is generated. Preferably, the preset number in accumulator 52 will be able to be varied by the physician.

The bradycardia condition sensing circuit shown in FIG. 2 includes a second oscillator controlled counter 54. Oscillator control counter 54 is similar to counter 50 and preferably also counts to approximately 15,500. Resistor R2 and capacitor C2 are selected so that the counter 54 counts to the second predetermined number (approximately 15,500) at a second predetermined rate of approximately 13,000 counts per second. This is the equivalent of a heartbeat rate of approximately 50 beats per minute or a time duration between beats of approximately 1200 milliseconds. The reset input to the oscillator counter 54 is also connected to the pulse generator 32 so that the same is reset to zero each time a pulse is received from the pulse generator 32. The oscillator counter 54 generates a second output signal each time it counts out without being reset and applies this second output signal to the clock input of a second counter accumulator 56.

It should be apparent to those skilled in the art that the oscillator counter 54 will only reach its full count and thereby increment counter accumulator 56 if the pulse rate from the pulse train generated by pulse generator 32 is less than 50 beats per minute, i.e. a time duration between pulses of greater than 1200 milliseconds. Again, in order to prevent the device from being too sensitive, the counter accumulator 56 is preset so that a second control signal is generated on control line 38 only if the accumulator is incremented to a preselected second preset number such as eight. As with the first oscillator counter 50 and the first counter accumulator 52, the second oscillator counter 54 and the second counter accumulator 56 are variable so that the physician can change the pulse rate which will be considered to be a bradycardia condition and can change the number of second output signals from the oscillator counter 54 which are needed in order to increment the counter accumulator 56 to generate a bradycardia control signal.

The present invention may be embodied in other specific forms without departing from the spirit or essential attributes thereof and accordingly reference should be made to the appended claims rather than to the foregoing specification as indicating the scope of the invention.

I claim:
1. An ambulatory arrhythmia detection and ECG recorder adapted to be carried by a patient comprising:
   (A) a plurality of electrodes adapted to be placed on the patient's body for developing electrical signals indicative of the patient's cardiac rhythm;
   (B) amplifier and filter means connected to said electrodes for amplifying and filtering said electrical signals;
   (C) recording means for recording the amplified and filtered electrical signals;
   (D) recorder controller means having a plurality of inputs, said controller means activating said recording means whenever a control signal is applied to one of its inputs;
   (E) timing means connected to said controller means and said recording means for deactivating said recording means after a preset time period has elapsed;
   (F) means for converting said amplified and filtered electrical signals into a pulse train wherein each pulse represents a different QRS complex in said electrical signals and is generated in real time with its respective QRS complex;
   (G) means for determining a tachycardia condition and being connected to one of said inputs to provide a first control signal thereto whenever a tachycardia condition is sensed;
   (H) said means for determining a tachycardia condition including:
      (i) a first oscillator controlled counter which counts at a first predetermined rate to a first predetermined number and which generates a first output signal each time it reaches said predetermined number;
      (ii) said first counter having a reset input and having said pulse train applied thereto so that said counter is reset upon the receipt of each pulse;
      (iii) a first accumulator having a reset input and a clock input, said reset input receiving said first output signals from said first counter to reset the accumulator each time a first output signal is received, said clock input receiving said pulse train to increment said accumulator each time a pulse is received, said accumulator producing said first conrol signal whenever the same is incremented to a first preset number;
   (I) means for determining a bradycardia condition and being connected to another of said inputs to provide a second control signal thereto whenever a bradycardia condition is sensed, said means for determining a bradycardia condition including:
      (i) a second oscillator controlled counter which counts at a second predetermined rate to a second predetermined number and which generates a second output signal each time it reaches said predetermined number;
      (ii) said second counter having a reset input and having said pulse train applied thereto so that said counter it reset upon receipt of each pulse;
      (iii) a second accumulator having a clock input receiving said second output signals to increment said second accumulator each time a second output signal is received, said second accumulator producing said second control signal whenever the same is incremented to the second preset number.

2. The invention as claimed in claim 1 including means for varying said first and second predetermined counting rates.

3. The invention as claimed in claim 1 wherein said first predetermined rate and said first predetermined number are selected such that said first counter counts to said number in approximately 500 milliseconds.

4. The invention as claimed in claim 1 wherein said second predetermined rate and said second predetermined number are selected such that said second counter counts to said number in approximately 1200 milliseconds.

5. The invention as claimed in claim 1 including means for varying said first and second preset numbers of said accumulators.

6. The invention as clamined in claim 1 including means for frequency modulating said electrical signals before they are recorded.

7. The invention as claimed in claim 1 wherein said amplifier and filter means includes a high-pass filter for filtering out low frequency base line drift.

8. The invention as claimed in claim 1 wherein said amplifier and filter means includes a low-pass filter for removing artifacts from said signals.

9. The invention as claimed in claim 1 wherein said means for converting includes a means for differentiating the QRS complex of said signal and a pulse generator.

10. The invention as claimed in claim 1 further including means for manually applying a control signal to said controller to activate said recording means.

11. The invention as claimed in claim 1 further including means for automatically applying a control signal to said controller to activate said recording means at predetermined intervals.

12. The invention as claimed in claim 11 further including means for selecting one of a plurality of different intervals.

13. The invention as claimed in claim 1 wherein said recording means includes a magnetic tape recorder.

* * * * *